United States Patent
Gal et al.

(10) Patent No.: US 7,817,827 B2
(45) Date of Patent: Oct. 19, 2010

(54) ENHANCED PLANAR SINGLE PHOTON EMISSION IMAGING

(75) Inventors: Yaniv Gal, Haifa (IL); Jacob Oaknin, Kfar Yona (IL); Shoulamit C. Shwartz, Atlit (IL); Israel Ohana, Haifa (IL)

(73) Assignee: Ultraspect Ltd., Haifa (IL)

( * ) Notice: Subject to any disclaimer, the term of this patent is extended or adjusted under 35 U.S.C. 154(b) by 890 days.

(21) Appl. No.: 10/560,946

(22) PCT Filed: Jun. 20, 2004

(86) PCT No.: PCT/IL2004/000545
§ 371 (c)(1),
(2), (4) Date: Mar. 12, 2007

(87) PCT Pub. No.: WO2004/113951
PCT Pub. Date: Dec. 29, 2004

(65) Prior Publication Data
US 2007/0217666 A1    Sep. 20, 2007

(30) Foreign Application Priority Data
Jun. 22, 2003   (IL) .................................. 156569

(51) Int. Cl.
*G06K 9/00* (2006.01)
(52) U.S. Cl. .................. 382/128; 378/25; 358/519; 250/269.3
(58) Field of Classification Search .............. 382/100, 382/128, 130, 131, 132; 128/922; 378/4–27; 358/519; 250/269.3, 269.6, 269.7, 370.08, 250/370.09
See application file for complete search history.

(56) References Cited

U.S. PATENT DOCUMENTS

| | | | |
|---|---|---|---|
| 4,149,249 A * | 4/1979 | Pavkovich | 378/14 |
| 4,873,632 A | 10/1989 | Logan et al. | |
| 5,376,795 A | 12/1994 | Hasegawa et al. | |
| 5,567,944 A * | 10/1996 | Rohe et al. | 250/370.09 |
| 6,178,223 B1 * | 1/2001 | Solomon et al. | 378/62 |
| 6,324,249 B1 * | 11/2001 | Fazzio | 378/22 |
| 6,507,633 B1 | 1/2003 | Elbakri et al. | |
| 6,792,203 B1 * | 9/2004 | Ide et al. | 396/65 |
| 6,943,355 B2 | 9/2005 | Shwartz et al. | |
| 7,099,503 B2 * | 8/2006 | Nishide | 382/131 |
| 7,667,203 B2 * | 2/2010 | Hindi et al. | 250/363.01 |
| 2007/0153972 A1 * | 7/2007 | Fujishige et al. | 378/19 |

* cited by examiner

*Primary Examiner*—Anand Bhatnagar
(74) *Attorney, Agent, or Firm*—Pearl Cohen Zedek Latzer, LLP

(57) ABSTRACT

An apparatus and method for obtaining a planar image of a portion (4) of a body (5) and enhancing image quality of at least one specific organ or volume of interest located within the portion (4) of the body (5), administered with radiopharmaceutical substance radiating gamma rays, by using single photon emission imaging, for determination of functional information thereon, comprising: (a) acquiring at least one projection data of the portion (4), by means of a gamma camera detector (2); (b) determining the effective distance between the detector (2) and the specific organ of interest; (c) calculating weight values taking into account acceptance angles of the gamma camera detector (2) and the effective distance; and (d) obtaining a two dimensional image of a spatial distribution of the pharmaceutical substance within the portion (4) by mathematically analyzing the data in conjunction with weight values.

18 Claims, 7 Drawing Sheets

ENHANCED PLANAR SINGLE PHOTON EMISSION IMAGING

FIELD OF THE INVENTION

The present invention relates to a nuclear medicine imaging. More particularly it relates to enhancing planar single photon emission imaging.

BACKGROUND OF THE INVENTION

Single photon emission (SPE) imaging is a known medical imaging technique. It involves injecting radiopharmaceutical substance into a patient's body and evaluating the distribution of the radiopharmaceutical substance, which is indicated by the distribution of gamma rays emitted from within the patient's body.

A radiation-detecting system, often referred to as Gamma camera, detects those gamma rays. Gamma camera detects gamma rays emitted from the radiopharmaceuticals substances, and the data acquired is analyzed to form an image representing the distribution of concentrations of the radiopharmaceutical substance within a specific body area.

Several modalities of SPE imaging are in use:

One of them is Single Photon Emission Computerized Tomography (SPECT). In this technique the gamma camera rotates around the region of interest of the patient's body, and data are collected at several angular positions (hereafter referred to as angular projections). A fully three dimensional image is formed.

SPECT is considered to be a very useful technique and a good tool for obtaining diagnostic information, however it requires the collection of large number of emitted photon (large statistics) and this means that in order to obtain the required number of photons, a long acquisition time is necessary. Long acquisition time means that the patient is subjected to a relatively long period of discomfort and furthermore, making the overall number of patients who can be imaged in a given time relatively small—a feature that many medical institutes and hospitals regard as extremely unfavorable and undesirable.

In order to reduce acquisition time planar or static imaging technique is sometimes used.

Unlike SPECT, in planar imaging techniques, the detector is kept at a fixed angular position in relation to the patient's body. The formed image is essentially a two-dimensional single projection of the administered radiopharmaceutical substance concentration within the patients body and lacks the three-dimensional information provided by SPECT (more than one projection may be acquired, but each projection is treated separately, yielding a single image).

The popularity of static nuclear imaging stems from the shorter time it takes to acquire an image, possibly reduced radiation exposure and reduced discomfort to the patient. Shorter imaging time enables scanning of large portions, or even the full length, of the patient's body, by either obtaining several images, possibly partially overlapping, or by slowly moving the camera along the patient body. Sometimes, several consecutive images of the same portion of the patient's body are taken in order to allows the physician to follow the dynamic redistribution of radiopharmaceutical substance in it, and assess the functioning of organs.

In prior art planar imaging, the image is in fact a representation of the distribution of incident photons across the gamma camera detector, without any additional image processing or with general image processing techniques, for example smoothing, which are pure mathematical manipulations of the collected data regardless of the physical nature of the system. In other words, if a planar single photon emission image undergoes any image processing, this processing does not take into account any physical parameters associated with the system (the nature of radiopharmaceutical substances and the patient's anatomy).

Gamma camera generally comprises a photon detector crystal coupled with a plurality of photomultiplier tubes, or an array of solid-state detectors combined with position logic circuits and data analysis apparatus. A collimator for limiting the angle of incident gamma rays may be incorporated with the gamma camera. Collimators are used to limit the detection of photons to a predetermined range of incidence angles (photons with greater incidence angles are absorbed by the collimator septa). A collimator typically includes thousands of squares, round or hexagonal parallel channels, through which, and only through which, gamma rays are allowed to travel and reach the detector. Generally, a parallel-hole collimator is in use, however various other arrangements may be used.

As gamma rays are emitted from the radiopharmaceutical substance, they travel through the collimator, unabsorbed and interact with the detector, which is placed directly adjacent to the collimator. The interactions of the gamma rays with the detector crystal create flashes of light in a process called scintillation. The scintillation light is preferably detected by an array of photomultiplier tubes, which are normally coupled to the back of the crystal. Photomultiplier tubes are used when a very small amount of light is emitted in scintillation. The output signals from the photomultiplier tubes are electric pulses, proportional to the energy of the gamma rays. The electric pulse output is received by position logic circuits, which determine the position where the scintillation event had occurred on the detector. Similarly, in solid-state detectors including solid-state crystals, the incident photons produce electric current corresponding to the energy of the incident photon in the specific location of incidence. This current is picked up by electrodes coupled to the solid-state crystals and is processed. The data is processed by position logic circuits and is transferred to a processing computer in order to process the data into readable image of the spatial distribution of the radiopharmaceutical substances within the patient's body. The main limitations to the quality of SPE images comes from:

A) Geometric resolution of the collimator. Getting information about the location where a photon was emitted requires limiting the incidence angle of those accepted for detection within predetermined ranges. The narrower the range, the better the resolution, but also the fewer the number of collected photons. Resolution is thus limited by sensitivity, and vice versa. High-resolution collimators typically used in the art reject photons at angles larger than 2 degrees, while high-sensitivity collimators reject those at angles larger than 3 degrees. The camera spatial resolution depends on the geometric resolution of the collimator, and degrades with distance between the surface of the collimator and the organ being imaged.

B) Limited number of registered gamma ray photons. a) The constraints imposed on the sensitivity of the collimator by geometrical resolution needs (typically only 1, out of every 10,000 emitted photons, is collected), b) the low doses of radiopharmaceutical that can be administered to patients due to hazards associated to exposure to gamma radiation, c) limited acquisition time.

All three factors limit the number of registered photons. This together with the random nature of radioactive decay turns the data into only a statistical (noisy) representation of the actual activity within the body of the patient.

Gamma ray photons, particularly of high energy, have some probability of penetrating the collimator septa, and reaching the detector even though their angle of incidence exceeds the collimator acceptance angle.

Gamma ray detectors have finite resolution. The ability of the position logic circuits in a scintillation camera to determine the precise position of a scintillation event is primarily determined by the number of photons generated in the crystal by this event, and thus the detector resolution strongly depends on the gamma ray energy. In multi-crystal detectors, resolution mainly depends on the size of the individual crystals.

Compton scattering within the patient, in the collimator or in the detector may cause a gamma ray photon to be registered in an erroneous place.

U.S. Pat. No. 4,873,632 (Logan, et al), titled *APPARATUS AND METHODS FOR SCATTER REDUCTION IN RADIATION IMAGING*, filed in 1990, discloses discrimination of counted photons based on measured energy, using the energy information for correction of scattering and smoothing the resulted image to reduce noise. Iterative reconstruction methods are used for SPECT. U.S. Pat. No. 6,943,355 to the same assignee discloses a method for image reconstruction that results in enhanced three-dimensional nuclear image.

It is an object of the present invention to provide an image (hereinafter also referred to as—planar image) representing two-dimensional projection of the three-dimensional distribution of radiopharmaceutical substance administered to a patient.

It is another object of the present invention to provide a method for enhancing planar nuclear images.

It is an object of the present invention to provide a gamma camera adapted to enhance planar single photon emission imaging.

It is another object of the present invention to provide a gamma camera adapted to provide a shorter acquisition time and thus relatively reducing the discomfort of a patient.

Yet another object of the present invention is to provide a gamma camera having improved image sensitivity and resolution.

Still another object of the present invention is to provide a gamma camera having improved lesion detectability.

Furthermore, it is another object of the present invention to provide a method for enhancing the quality of planar single photon emission imaging.

Furthermore, it is another object of the present invention to provide planar single photon emission imaging obtained from relatively smaller amount of radiopharmaceutical substances.

Furthermore, it is another object of the present invention to provide planar single photon emission imaging having reduced image-processing time.

More objects and advantages of the present invention will become apparent from the following detailed descriptions when read in conjunction with the accompanying drawings.

SUMMARY OF THE INVENTION

There is thus provided, in accordance with some preferred embodiments of the present invention, a method of enhancing image quality of a planar nuclear emission image acquired by a gamma camera, comprising the steps of:

(a) calculating weight values taking into account the physical configuration of the gamma camera;

(b) generating a two dimensional image of a spatial distribution of the pharmaceutical substance within the portion of the body by mathematically analyzing the acquired image in conjunction with the weight values.

Furthermore, in accordance with some preferred embodiments of the present invention, there is provided a method of obtaining a planar image of a portion of a body and enhancing image quality of at least one specific organ or volume of interest located within the portion of the body, administered with radio-pharmaceutical substance radiating gamma rays, by using single photon emission imaging, for determination of functional information thereon, comprising the steps of:

(a) acquiring at least one projection data of said portion of the body, by means of a gamma camera detector;

(b) determining the effective distance between the detector and the specific organ of interest;

(c) calculating weight values taking into account acceptance angles of the gamma camera detector and the effective distance;

(d) obtaining a two dimensional image of a spatial distribution of the pharmaceutical substance within the portion of the body by mathematically analyzing said data in conjunction with weight values.

Furthermore, in accordance with some preferred embodiments of the present invention, the step of calculating weights values is taking into account the probability of a photon to be attenuated within the body.

Furthermore, in accordance with some preferred embodiments of the present invention, a collimator with septa is used adjacent the detector, and the step of calculating weights values is taking into account the probability of a photon to penetrate the septa of the collimator.

Furthermore, in accordance with some preferred embodiments of the present invention, the steps of acquiring the data projection comprises acquiring data relating to two opposing projections.

Furthermore, in accordance with some preferred embodiments of the present invention, mathematically analyzing said data is done using iterative algorithm.

Furthermore, in accordance with some preferred embodiments of the present invention, said iterative algorithm is applied at least in one of the iterations to a subset of the acquired data.

Furthermore, in accordance with some preferred embodiments of the present invention, said iterative algorithm is applied to data collected in list mode.

Furthermore, in accordance with some preferred embodiments of the present invention, the determination of effective distance is done relaying on a priory knowledge of human anatomy.

Furthermore, in accordance with some preferred embodiments of the present invention, the determination of effective distance is done relaying on patient measurements.

Furthermore, in accordance with some preferred embodiments of the present invention, the determination of effective distance is done relaying on single photon emission image taken from another detector position.

Furthermore, in accordance with some preferred embodiments of the present invention, the determination of effective distance is done relaying on other medical imaging modality.

Furthermore, in accordance with some preferred embodiments of the present invention, the other medical imaging modality is selected from the group of X-Ray, CT, MRI, PET and Ultrasound imaging.

Furthermore, in accordance with some preferred embodiments of the present invention, two projections data of said portion of the body are acquired from positions that are substantially opposite to each other.

Furthermore, in accordance with some preferred embodiments of the present invention, said two projections data are acquired using two dissimilar collimators.

Furthermore, in accordance with some preferred embodiments of the present invention, the effective distance for processing data from both projections is half the distance between detector faces in said positions.

Furthermore, in accordance with some preferred embodiments of the present invention, the effective distance associated with each is different.

Furthermore, in accordance with some preferred embodiments of the present invention, the effective distance varies across the portion of the body.

Furthermore, in accordance with some preferred embodiments of the present invention, the effective distance varies across the portion of the body in such a way that voxels residing at said effective distance form a plane inclined to the surface of a detector.

Furthermore, in accordance with some preferred embodiments of the present invention, the effective distance varies across the portion of the body in such a way that the voxels residing at said effective distance form a contiguous curved surface.

Furthermore, in accordance with some preferred embodiments of the present invention, the effective distance varies across the portion of the body in such a way that the vixels residing at said effective distance form a non-contiguous surface.

Furthermore, in accordance with some preferred embodiments of the present invention, the detector is adapted to detect emitted photons having incident angles in the range of 0 to more than 5 degrees.

Furthermore, in accordance with some preferred embodiments of the present invention, the detector is adapted to detect emitted photons having incident angles in the range of 0 to about 90 degrees.

Furthermore, in accordance with some preferred embodiments of the present invention, distances between different discrete elements of the portion of the body and corresponding discrete elements of the projection of the portion of the body on the detector substantially determined by the average distance between the detector and the organ to be imaged in the patient.

Furthermore, in accordance with some preferred embodiments of the present invention, said reconstructing an image by processing said data comprises the steps of:

(a) dividing an area of the detector facing the body into M bins;

(b) dividing the portion of the body into N voxels;

(c) providing a set of values $D_i$ (wherein i=1, ... ,M) reflective of the number of photons acquired by each bin;

(d) constructing a matrix P having matrix elements $P_{i,j}$ of weight values of the voxels of the portion of the body (wherein i=1, ... ,M and j=1, ... ,N), the matrix P setting a relation between each bin of the detector and each voxel of the portion of the body;

(e) modeling a relation between said set of values $D_i$ and a set of voxel values $V_j$ of said image and deriving said set of voxel values $V_j$ of said image, whereby said spatial distribution of the pharmaceutical substance indicating the functional information on said portion of the body is obtained.

Furthermore, in accordance with some preferred embodiments of the present invention, said bins are all equal in size.

Furthermore, in accordance with some preferred embodiments of the present invention, said bins are not of equal size.

Furthermore, in accordance with some preferred embodiments of the present invention, said voxels are all equal in size.

Furthermore, in accordance with some preferred embodiments of the present invention, said voxels are not of equal in size.

Furthermore, in accordance with some preferred embodiments of the present invention, dimensions of said bins are unequal to the dimensions of pixels in the obtained image.

Furthermore, in accordance with some preferred embodiments of the present invention, the step of modeling a relation between said set of values $D_i$ and a set of voxel values $V_j$ of said image and deriving said set of voxel values $V_j$ of said image comprises the step of solving a set of equations $$D_i = \sum_{j=1}^{N} P_{i,j} V_j$$

with respect to each value $V_j$, (wherein i=1, ... ,M).

Furthermore, in accordance with some preferred embodiments of the present invention, the step of modeling a relation between said set of values $D_i$ and a set of voxel values $V_j$ of said image and deriving said set of voxel values $V_j$ of said image comprises the step of solving a set of equations $$D_i = \sum_{j=1}^{N} P_{i,j} V_j + E_i$$

with respect to each value $V_j$, wherein $E_i$ is a set of measurement errors.

Furthermore, in accordance with some preferred embodiments of the present invention, the step of modeling a relation between said set of values $D_i$ and a set of voxel values $V_j$ of said image and deriving said set of voxel values $V_j$ of said image comprises the step of solving an optimization problem for estimating a mean value $\lambda(V_j)$ of random variables $V_j$, using the $D_i$ values measured by the detector.

Furthermore, in accordance with some preferred embodiments of the present invention, said random variables $V_j$ are Gaussian random variables.

Furthermore, in accordance with some preferred embodiments of the present invention, said random variables $V_j$ are Poisson random variables.

Furthermore, in accordance with some preferred embodiments of the present invention, estimating the mean value $\lambda(V_j)$ of the random variables $V_j$, is carried out by calculating a maximum of the likelihood function.

Furthermore, in accordance with some preferred embodiments of the present invention, $$L[\lambda(D_i)] = \prod_{i=1}^{M} \frac{e^{-\lambda(D_i)} \lambda(D_i)^{D_i}}{D_i!},$$

with respect to the unknowns $V_j$.

Furthermore, in accordance with some preferred embodiments of the present invention, the step of modeling a relation between said set of values $D_i$ and a set of voxel values $V_j$ of said image and deriving said set of voxel values $V_j$ of said image comprises the step of solving a Bayesian optimization problem utilizing a likelihood and penalty functions.

Furthermore, in accordance with some preferred embodiments of the present invention, the Bayesian optimization problem has the general form $V=\arg\max\{L[\lambda(D_i)]+\alpha F(V_j, V_k)\}$, where $\alpha$ is the weight that is given to the penalty function F.

Furthermore, in accordance with some preferred embodiments of the present invention, the matrix P is a matrix in which each of the matrix elements $P_{i,j}$ is a function of an average distance and solid angle at which a detector bin having an index i is viewed from the voxel having an index j.

Furthermore, in accordance with some preferred embodiments of the present invention, the matrix P is a matrix in which each of the matrix elements $P_{i,j}$ is a function of an average solid angle at which a detector bin having an index i is viewed from the voxel having an index j.

Furthermore, in accordance with some preferred embodiments of the present invention, the matrix P is a matrix in which each of the matrix elements $P_{i,j}$ is a function of an average distance and solid angle at which a voxel having an index j is viewed from a detector bin having an index i.

Furthermore, in accordance with some preferred embodiments of the present invention, the matrix P is a matrix in which each of the matrix elements $P_{i,j}$ is function of an average solid angle at which a voxel having an index j is viewed from a detector bin having an index i.

Furthermore, in accordance with some preferred embodiments of the present invention, the matrix P is a matrix in which each of the matrix elements $P_{i,j}$ is a function of a solid angle and distance at which a detector bin having an index i is viewed from a center of a voxel having an index j.

Furthermore, in accordance with some preferred embodiments of the present invention, the matrix P is a matrix in which each of the matrix elements $P_{i,j}$ is a function of a solid angle at which a detector bin having an index i is viewed from a center of a voxel having an index j.

Furthermore, in accordance with some preferred embodiments of the present invention, the matrix P is a matrix in which each of the matrix elements is a function of a solid angle and distance at which a center of a voxel having an index j is viewed from a detector bin having an index i.

Furthermore, in accordance with some preferred embodiments of the present invention, the matrix P is a matrix in which each of the matrix elements $P_{i,j}$ is a function of a solid angle at which a center of a voxel having an index j is viewed from a detector bin having an index i.

Furthermore, in accordance with some preferred embodiments of the present invention, the modeling of the relation between said set of values $D_i$ and a set of voxel values $V_j$ of said image, is biased by an attenuation effect of the patient body.

Furthermore, in accordance with some preferred embodiments of the present invention, the matrix P is a matrix in which each of the matrix elements $P_{i,j}$ is influenced by the attenuation density that exists on the path of the photons that emanate at voxel j and arrive at bin i, for each detector position k.

Furthermore, in accordance with some preferred embodiments of the present invention, the matrix P is a matrix in which each of the matrix elements $P_{i,j}$ is influenced by the attenuation density that exists on the path of the photons that emanate at voxel j and arrive at bin i, for each detector position k and for each energy peak of the radio-pharmaceutical substance that is used.

Furthermore, in accordance with some preferred embodiments of the present invention, the method further comprises the step of providing a collimator between said portion of body and said detector, and wherein the matrix P is a matrix in which each of the matrix elements $P_{i,j}$ is multiplied by the area of bin i that can be seen from voxel j through the collimator.

Furthermore, in accordance with some preferred embodiments of the present invention, said detector is adapted to move relative to the body.

Furthermore, in accordance with some preferred embodiments of the present invention, the step of calculating weight values involves taking into account probability of photon to undergo Compton scattering by within the body of the patient.

Furthermore, in accordance with some preferred embodiments of the present invention, the step of calculating weight values involves taking into account probability of photon to penetrate trough a septa of the collimator.

Furthermore, in accordance with some preferred embodiments of the present invention, the step of calculating weight values involves taking into account energy of the emitted photon.

Furthermore, in accordance with some preferred embodiments of the present invention, the step of calculating weight values involves taking into account measured energy of the detected photon.

Furthermore, in accordance with some preferred embodiments of the present invention, the step of calculating weight values involves taking into account both energy of the emitted photon and the measured energy of the detected photon.

Furthermore, in accordance with some preferred embodiments of the present invention, the step of calculating weight values involves taking into account camera imperfections associated with specific bin.

Furthermore, in accordance with some preferred embodiments of the present invention, said at least one crystal is a semiconductor crystal.

Furthermore, in accordance with some preferred embodiments of the present invention, said detector includes at least a pair of septa mounted along an axis of the detector, the septa provided for limiting the field of view.

Furthermore, in accordance with some preferred embodiments of the present invention, plurality of planar images are obtained each with different set of weights.

Furthermore, in accordance with some preferred embodiments of the present invention, said plurality of different sets of weights are calculated taking into account plurality of effective distances.

Furthermore, in accordance with some preferred embodiments of the present invention, said plurality of different set of weights are calculated taking into account plurality of emitted photon energies.

Furthermore, in accordance with some preferred embodiments of the present invention, said plurality of different set of weights are calculated taking into account plurality of detected photon energy ranges.

Furthermore, in accordance with some preferred embodiments of the present invention, said plurality of obtained planar images are displayed side by side.

Furthermore, in accordance with some preferred embodiments of the present invention, plurality of planar images are displayed one after the other.

Furthermore, in accordance with some preferred embodiments of the present invention, at least two obtained images are combined to form combined image.

Furthermore, in accordance with some preferred embodiments of the present invention, at least two obtained images are combined to form combined image by averaging the at least two obtained images.

Furthermore, in accordance with some preferred embodiments of the present invention, at least two obtained images are combined to form combined image by weighted average.

Furthermore, in accordance with some preferred embodiments of the present invention, coefficients of said weighted average are stored in an averaging coefficients map.

Furthermore, in accordance with some preferred embodiments of the present invention, coefficients of averaging coefficients map are determined by statistical analysis of the quality of obtained images.

Furthermore, in accordance with some preferred embodiments of the present invention, distances between different discrete elements of the portion of the body and corresponding discrete elements of the projection of the portion of the body on the detector substantially determined by the average distance between the detector and the organ to be imaged in the patient.

Furthermore, in accordance with some preferred embodiments of the present invention, there is provided an apparatus for obtaining a planar image of a portion of a body and enhancing image quality of at least one specific organ or volume unit of interest located within the portion of the body, administered with radio-pharmaceutical substance radiating gamma rays, by using single photon emission imaging, for determination of functional information thereon, comprising:

(a) a detector adapted to detect photons emitted from said portion of the body, said detector having at least one photon detector crystal, the detector adapted to convert photons into electric signals;

(b) a position logic circuitry for processing said electric signals and thereby deriving there from data indicative of positions on said photon detector crystal, where the photons have impinged the detector;

(c) a data analysis processor for obtaining an image of a spatial distribution of the radiopharmaceutical substance within said portion of the body by processing said data and in conjunction with weight values derived taking into account the physical configuration of the gamma camera;

(d) obtaining a two dimensional image of a spatial distribution of the pharmaceutical substance within the portion of the body by mathematically analyzing said data in conjunction with weight values.

Furthermore, in accordance with some preferred embodiments of the present invention, an image enhancing processor is further provided communicating with the data analysis processor.

Furthermore, in accordance with some preferred embodiments of the present invention, the detector is adapted to detect photons having incident angles in the range of 0 to more than 5 degrees.

Furthermore, in accordance with some preferred embodiments of the present invention, the detector is adapted to detect photons having incident angles in the range of 0 to more than 10 degrees to reach the detector.

Furthermore, in accordance with some preferred embodiments of the present invention, the detector is adapted to detect photons having incident angles in the range of 0 to about 90 degrees.

Furthermore, in accordance with some preferred embodiments of the present invention, said at least one crystal is a semiconductor crystal.

Furthermore, in accordance with some preferred embodiments of the present invention, said semiconductor crystal is a crystal selected from the group consisting of Cadmium-Telluride (CdTe), Cadmium-Zinc-Telluride (CeZnTe) and Lead Iodine (PbI).

Furthermore, in accordance with some preferred embodiments of the present invention, said detector includes at least a pair of septa mounted along an axis of the detector, the septa provided for limiting the field of view.

Furthermore, in accordance with some preferred embodiments of the present invention, the detector is provided with a collimator having holes that are symmetric, such as circular, square or hexagonal shaped holes.

Furthermore, in accordance with some preferred embodiments of the present invention, the detector is provided with a collimator having direction bias holes favoring detection from a predetermined frontal direction and limiting detection from other directions.

Furthermore, in accordance with some preferred embodiments of the present invention, the detector is provided with a collimator having non-symmetric holes.

Furthermore, in accordance with some preferred embodiments of the present invention, the detector is provided with a collimator having holes of different dimensions along different axes, such as ellipse or rectangular shape holes.

Furthermore, in accordance with some preferred embodiments of the present invention, the detector is provided with a collimator having bores of cylindrical, conic or other converging or diverging shapes.

Furthermore, in accordance with some preferred embodiments of the present invention, the detector is provided with a collimator having bores of different shape or size or both.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF THE INVENTION AND PREFERRED EMBODIMENTS

Figure 1:
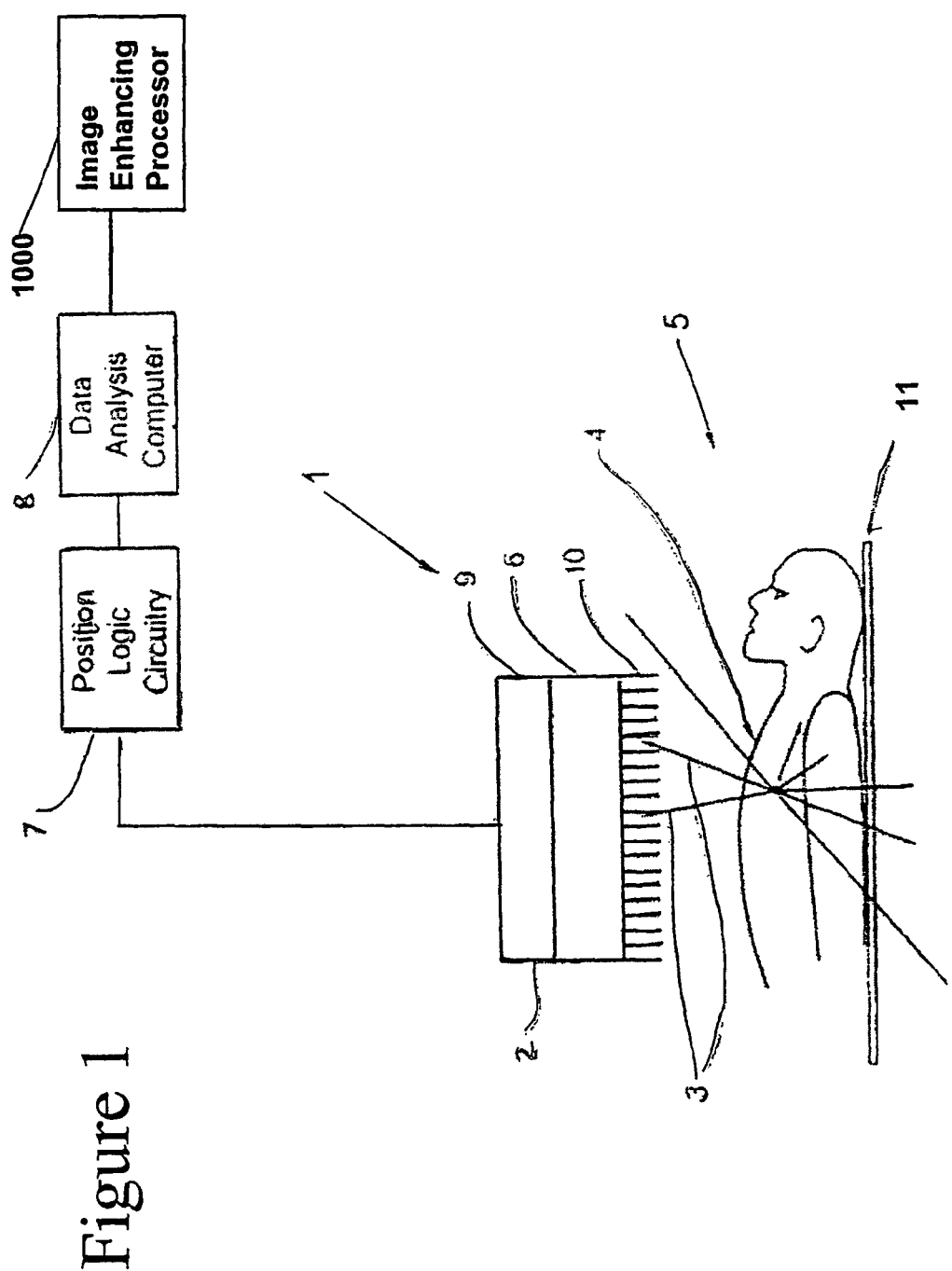
FIG. 1 illustrates a general view of a gamma camera for enhanced planar single photon emission imaging, in accordance with a preferred embodiment of the present invention.

The general object of the present invention, which will be described subsequently in greater detail, is to provide a novel technique for acquisition and reconstruction of planar single photon emission images.

Standard planar single photon emission imaging merely collects data from a single angular position, and displays the resulting 2D projection of the imaged body. Thus, it fails to take into account any particulars of the imaging system The technique of the present invention, conversely, makes use of available information regarding the physical conditions on which emitted photons are collected by the gamma camera, for example: a) a detailed description of the collimator used, if any; b) a detailed account of the positioning of the camera with respect to the patient's body; c) distance from the patient's body to the camera; d) attenuation map of the patient's body, if available; e) energy of the gamma rays; f) Compton scattering within the patient or the detector.

The present invention is based on a correct account of all the directions from which gamma rays might reach the detector, positioned at selected angular positions in relation to the patient's body. This is achieved by taking into consideration the likelihood that photons emitted from parts of the examined organ would reach each position within the detector. It's customary to partition both the detector's surface and the patient's volume into a grid of discrete elements (referred hereafter as bins and voxels respectively). Such likelihood values (weights) then establish a coupling for each pair voxel/bin. According to the technique of the present invention such coupling values are chosen to, fully encompass all available information regarding the geometry of the acquisition system and the patient's anatomy. For example, they take into consideration the solid angle a bin is viewed from different voxels in the patient's body.

There is provided in accordance with the present invention, a method of obtaining and enhancing an image of the patient body, or a portion of it, from single photon emission data with the purpose of determination of functional information therein that makes use of the coupling weights just described. For example the method of least squares which can be solved by singular value decomposition.

In one exemplary embodiment the method comprises the following steps:

(a) acquiring photons emitted from said portion of the body, by means of a detector capable of converting the photons into electric signals, the detector having at least one crystal and adapted to detect emitted photons;

(b) processing said electric signals by a position logic circuitry and thereby transforming them into data indicative of positions on said photon detector crystal, where the photons have impinged the detector; and (c) iteratively reconstructing a two dimensional image of a spatial distribution of the pharmaceutical substance within the portion of the body by processing said data and taking into consideration weight values, which are functions of, at least, the angles and distances between different discrete elements of the portion of the body and corresponding discrete elements of the projection of the portion of the body on the detector.

The technique of the present invention may lead to substantial improvement in image resolution and improvement in image quality with respect to the conventional planar imaging technique. That may result in better lesion detectability, shorter acquisition time or administration of smaller doses of radio-pharmaceutical substances to the patient. Optionally, the use of iterative algorithm may reduce processing time.

The present invention seeks to exploit and further enhance the advantages of planar single photon emission imaging, namely considerably shorter acquisition time with respect to SPECT. Furthermore, it is asserted that the technique of the present invention may further reduce acquisition time of an image, and enhance resolution.

Standard planar single photon emission imaging simply collects the detected photons and displays their planar distribution on the detector. Optionally image smoothing may be applied, which is carried out in standard image smoothing techniques that fail to take into account the specific physical nature of the imaging system or the patient. This image smoothing, while appearing more pleasant to the eye further reduces the resolution of the image and hence reduces its clinical value.

Understanding that physicians are more than often interested in a certain organ within the patient's body, the inventors of the present invention assert that in order to enhance the resolution of the image obtained in planar single photon emission imaging, it is suggested to analyze the data on the detected photons assuming that it originated from one layer (or several layers) of the—patient's body, in which the specific organ (or portion of it) lies. The data is analyzed using mathematical model taking into account the "effective distance" between the organ and the detector (see further explanation relating to FIGS. 2 and 3).

The mathematical analysis takes into account a single projection (or dual opposing projections) data of said portion of the body, detected by the gamma camera detector and (optionally iteratively) enhancing a two dimensional image of a spatial distribution of the pharmaceutical substance within the portion of the body by processing said data in conjunction with weight values, derived from the effective distance, the physical configuration of the gamma camera and the patient. For example the configuration may comprise of: type of collimator used, detector properties or functions of either solid angles or solid angles and distances between different discrete elements of the portion of the body and corresponding discrete elements of the projection of the portion of the body acquired by the gamma camera.

An aspect of the present invention is the provision of a gamma camera and method for obtaining an enhanced planar nuclear imagining. An aspect of the present invention is the provision of a gamma camera used in a planar imaging technique for obtaining enhanced planar single photon emission imaging (of an organ or body system, following exposure to radiopharmaceutical substances), the gamma camera generally comprising: detector for detecting gamma rays emitted from the radiopharmaceutical substances within the patient's body, and converting the gamma rays into electric signals; a position logic circuitry that processes the electric signals in a way that the electric signals are transformed into data that indicates the position where the impinged event of the gamma rays occurred on the detector; a processing computer that processes said data into enhanced two-dimensional single photon emission imaging, illustrating spatial distribution of the radiopharmaceutical substance within the patient. The enhancing of the two-dimensional single photon emission imaging by the processing computer, involves using an algorithm that takes into consideration weight values, which are function of angles and distances, and sometimes additional elements as attenuation or scattering of the photons, between different discrete elements of the portion of the body and of corresponding discrete elements projection of the portion of the body on the detector. Therefore, correct account of gamma rays direction is achieved (this is explained in greater details hereinafter). The use of weight values in the obtaining of two-dimensional single photon emission imaging, greatly enhances the quality of nuclear medical imaging, with respect to known planar single photon emission imaging.

Reference is made to FIG. 1 depicting a side view of a simplified schematic diagram of gamma camera in accordance with the present invention, for obtaining a nuclear emission image of a portion of a body that has been administered by a radiopharmaceutical substance, which radiates gamma rays.

The gamma camera 1 comprises at least one detector 2 mounted in proximity to an inspected portion 4 of a body 5, a position logic circuitry 7 and a data analysis computer 8, all connected appropriately. Optionally, an image enhancing processor 1000 is connected to data analysis computer 8 via data communication link. In this optional configuration, when image enhancing is needed, acquired data, is transferred from data analysis computer to image enhancing processor. Image enhancing processor is optionally a digital processor specifically suitable for rapid data processing for example a powerful workstation, DSP or parallel data processor. Enhanced image (or plurality of enhanced images) is transferred from the image enhancing processor to the data analysis computer to be farther processed, stored or displayed.

Detector 2 includes at least one photon detector crystal 6 facing the portion 4 of body 5. The photon detector crystal 6 may be in the form of a semiconductor crystal or crystals. This crystal(s) may be selected from a first group including Cadmium-Telluride (CdTe), Cadmium-Zinc-Telluride (CeZnTe), Lead Iodine (PbI).

The detector 2 of the gamma camera 1 may further include at least one photo-multiplier 9. The photon detector crystal(s) in this case may be selected from a second group including Sodium Iodine (NaI), Bismuth Germanate (BGO), Yttrium Oxyorthosilicate (YSO), Cerium-doped Lutetium Oxyorthosilicate (LSO) and Cesium-Iodine (CsI). Alternatively, the light detection function of photo-multiplier 9 could be performed by solid-state photo-diode or avalanche photo-diode (APD).

The detector crystals listed above have different characteristics that are relevant for single photon emission imaging: they differ in their ability to resolve photon energy (also termed "energy resolution"), their internal spatial resolution and their stopping power. All of these characteristics affect the resolution and sensitivity of the resultant images. Therefore, nuclear gamma cameras utilizing different detector crystals will yield different resolution, using the same reconstruction algorithm.

Detector 2 may also be in the form of an array of photon detector crystals arranged in at least one row. The photon detector crystal array may be in the form of a plane or a ring surrounding the portion of the body. For example, detector 2 may be of the kind used in a known per se Anger camera.

Detector 2 may be capable of rotating around, or moving along, a desired trajectory relative to the body to acquire data at multiple predetermined positions from multiple views around the body. However, in a planar imaging, it is customary to have the detector (or all the detractors, if the gamma camera is equipped with more than one detector) at a fixed angle with respect to the body for the duration of the data acquisition. If the portion 4 to be imaged of the body 5 is larger than the gamma sensitive area of the detector 2, the detector is commonly moved relative to the body in steps as to take few possibly partially overlapping images or moved in a continuous manner.

The use of weights allows correction of detection systems imperfection and artifact.

For example, weights could be calculated taking into account the relative detection sensitivity of different location on the detector 2.

Specifically, in the case of solid-state gamma camera where each bin on the detector may have different probability to successfully detect an impinging gamma photon, the weights could be adjusted to take the sensitivity into account.

Similarly, artifact caused by using a collimator with non-uniform properties could be corrected by adjusting the weights accordingly.

Sensitivity maps are customary used in the art to correct fore these artifacts, however application of sensitivity map increases the noise in areas of reduced sensitivity.

Another type of artifact that may be corrected using proper weights are errors in the determination of the position of the gamma photon entrance point by the combination of detector/position logic. These systematic errors in position determination (known as linearity errors) could also be corrected by determining the values of the matrix P either from knowing the systematic behavior of the detector or by measuring the linearity corrections.

Generally, appropriate determination of the matrix elements P, could be used to correct for any systematic detection imperfection: position determination (linearity), Detection probability (sensitivity) and energy determination.

If large-hole collimator is used, a bin size smaller than the collimator bore size, the septa could "cast a shadow" over parts of the detectors and create artifact. Such artifacts were seen using collimator designed for high energy photons due to the large septa thickness. Using weights in accordance with the present invention may remove these artifacts.

Taking few sets of data while moving the detector slightly may assist the removal of small-scale irregularities in the detection system. Unlike simple dithering the detector that smoothes the image while specifying resolution, taking few sets of data while shifting the detector slightly between data set acquisition and associating each data set k with the matrix element $P_{i,j,k}$, may achieve artifact removal without scarifying resolution.

In a detector (for example a solid-state gamma camera), where the bin size may be larger then the desired resolution, sub-bin resolution may be achieved using the present invention. Dithering the detector by moving it at steps not equal to the bin size may assist achieving sub-bin resolution.

Angles of incidence of gamma rays from the portion 4 of the body 5 may be in the range from 0° to 90°. Detector 2 may be provided with means for establishing angles of incidence of gamma rays on the detector in a restricted range. It is noted that by angle of incidence it is meant the angle between the perpendicular to the surface of the detector and the ray path.

Such means may be in the form of appropriate collimator 10. However, these means should be such as to allow the gamma rays having various incident angles in the range of 0 to 3 or more degrees, and preferably, in the range of 0 to 10 or more degrees, to be detected. The collimator holes may be symmetric, such as circular or hexagonal shaped holes, or have different dimensions along the different axis, such as ellipse or rectangular shape holes. Furthermore, the shape of the bore of the collimators may be cylindrical, conic or other converging shapes.

In operation, detector 2 acquires radioisotope gamma ray photons 3, which are emitted from portion 4 of body 5 and passing through collimator 10. The gamma photons impinge the photon detector crystal 6. If the crystal 6 is a semiconductor crystal selected from the first group specified above, then the crystal converts the photons into electric signals, which are fed into a position logic circuitry 7 for processing. Alternatively, if the crystal is selected from the second group specified above, i.e. is of the kind that utilizing photo-multipliers, then the crystal converts photons 3 into scintillation light, which is, thereafter, transformed into electric signals by photo-multiplier 9.

As a result of the processing, the electric signals are transformed into data indicative of photon energy and positions on the photon detector crystal 6 in which the photons impinge the detector. The data that includes the position at which each photon impinged the detector is fed into a data analysis computer 8 for the purpose of processing, enhancing and displaying an image of a spatial distribution of the pharmaceutical substance within the portion of the body by processing said data. The photon energy information is registered for the assessment of the amount of Compton scattering that is introduced in the acquisition. In general, there is one energy window around each peak emission energy of the radio-pharmaceutical substance. The width of each window is preferably set as narrow as may be reasonable to the specific detector that is used, in order to reject as many scattered photons as possible.

Figure 2:
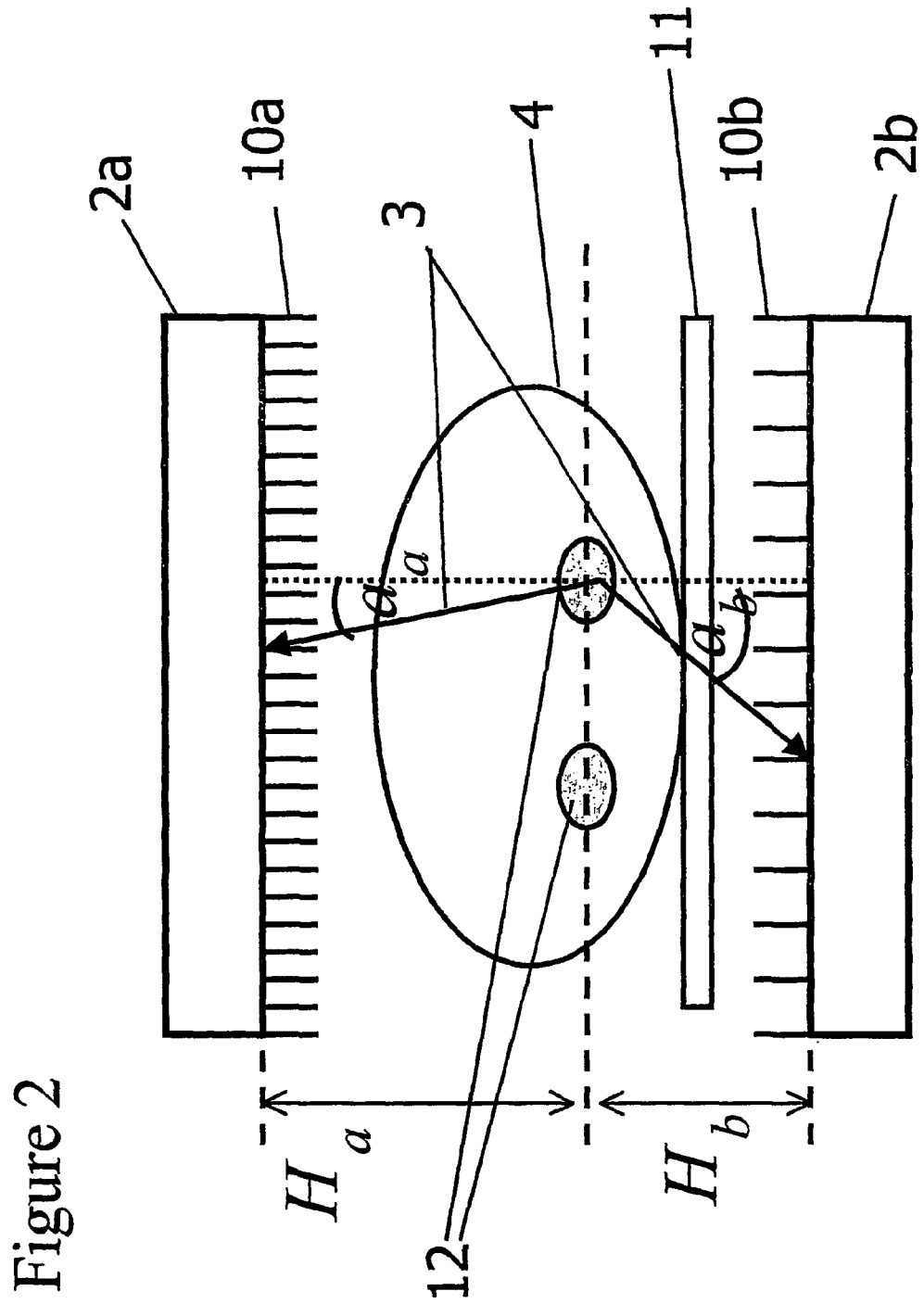
FIG. 2 illustrates a cross section of a gamma camera, in which two opposite detectors are positioned above and bellow a patient in accordance with a preferred embodiment of the present invention.

FIG. 2 shows a cross section of the gamma camera 1 and the portion of the body 4, showing two detectors 2a and 2b each equipped with collimators 10a and 10b respectively. In this exemplary illustration, one detector is placed above and the other detector is placed below the patient body, which is resting on a patient table 11 made of material having low gamma absorption properties. The use of more then one detector increases the sensitivity of the gamma camera and allows decreasing acquisition time. The detectors need not necessarily be positioned parallel to each other. It is sometimes advantageous to position the detectors at substantially right angle or at some other arbitrary angle to each other. In a camera equipped with more than one detector, collimator 10 may be chosen to have same, similar or different construction and photon angle restriction properties.

In many clinical examinations, the operator is interested in obtaining clinically relevant functional information about the patient's specific organ 12 or organs. Preferably, the detectors are positioned by the operator so as to minimize the distance to the specific organ 12. In this exemplary illustration, the distances from specific organ 12 (for example the patient's kidneys) to the first and second detectors are substantially equal to effective distance Ha and Hb respectively (it is noted that the organ has finite width and for sake of simplicity the distance may be considered to the center of the organ or consider the organ to be planar), although in the algorithm of the present invention the size of the organ might be taken into account with a "multi-slice" reconstruction procedure.

In the illustrated example of FIG. 2, the data taken by first detector 2a may differ from data taken by second detector 2b not only due to the random nature of radioactive emission, but mainly due to the difference in the distances between the distribution of radio-pharmaceutical substance in the body and the detectors and the degradation of resolution with respect to distance. Absorption and scattering of gamma photons in the body may affect differently the probability of a photon being detected and its trajectory.

Figure 3:
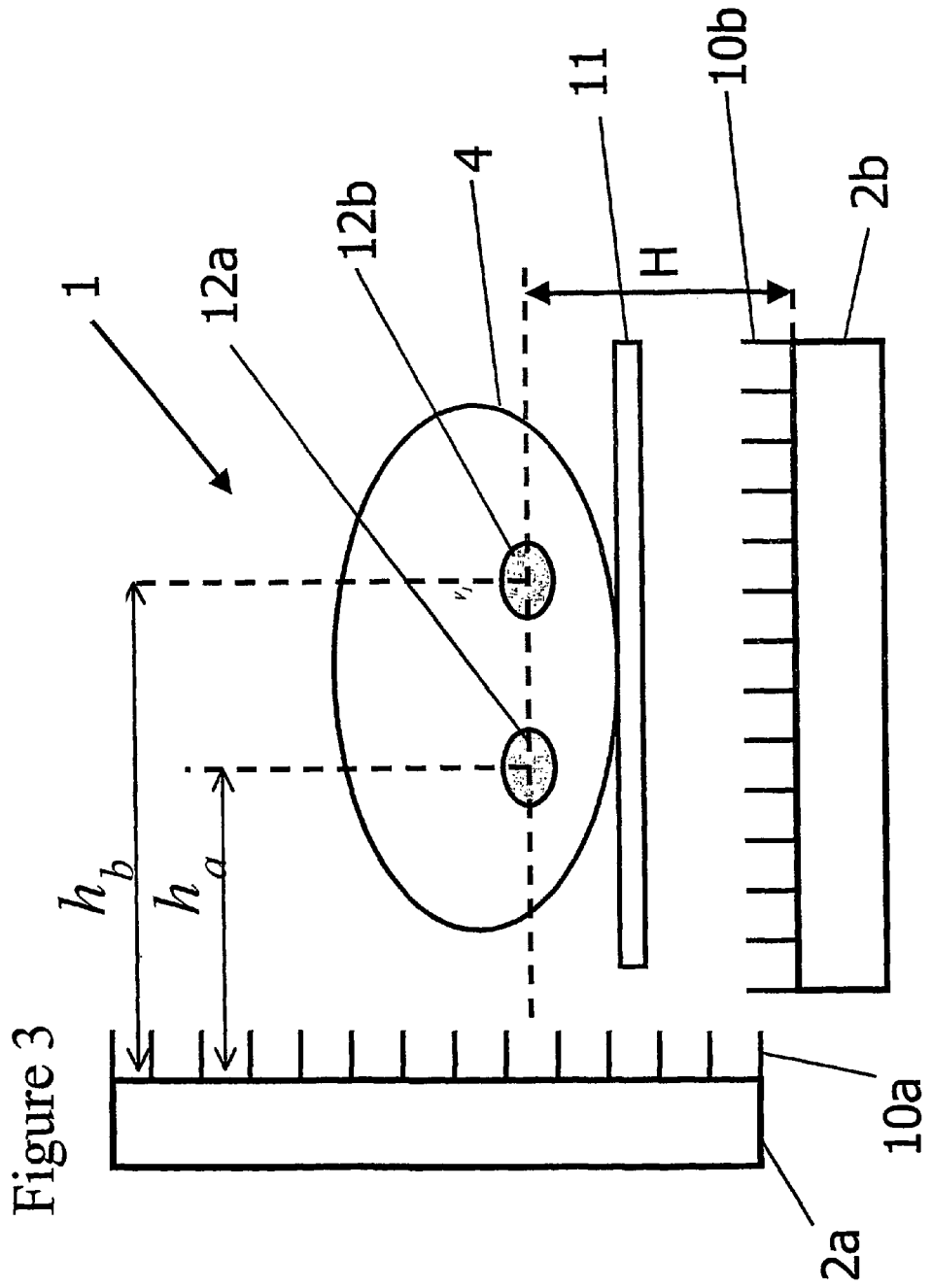
FIG. 3 illustrates a cross section of a gamma camera, in which the detectors are positioned in right angle with respect to each other, in accordance with another preferred embodiment of the present invention.

FIG. 3 shows a cross section of a gamma camera and portion of the body 4, showing detectors 2a and detector 2b positioned at substantially right angle to each other. In this exemplary illustration, one detector is placed substantially parallel to a plane intersecting with several specific organs. For example, when the kidneys of a patient are to be imaged, the detectors could be positioned so that the two kidneys are close, and at roughly the same distance from one of the detectors (detector 2b, below the patient lying on his back).

The effective distance H from specific organs 12a and 12b to detector 2b could be estimated from a planar image taken by detector 2a. Similarly, effective distances ha and hb from detector 2a and specific organ 12a and 12b respectively could be estimated by planar image taken by detector 2b. Estimation could preferably be made automatically using image processing algorithms as known in the art (such as calculation of "center of gravity" of the counted photons within a region or finding the bin with maximum number of counts or a segmentation method), or with operator intervention.

Alternatively or additionally the effective distance H between the specific organ and the detector can be estimated from common knowledge about human anatomy, by relaying on patient measurements such as dimensions or weight, or from other medical imaging modalities such as X-Ray, CT, MRI, PET, SPECT or ultrasonic imaging.

The enhancing of the image according to the present invention may be performed based on any appropriate existing algorithm, however, it is based on weight values, which are functions of either solid angles or solid angles and distances between different elements of the portion of the body and corresponding elements of body's projection on the detector.

For example, the enhancement of the image may start by dividing an area of the detector facing the body onto M bins and dividing portion 4 of body 5 onto voxels.

Since the goal of planar single photon emission imaging is to obtain a two dimensional image faithfully representing a two dimensional projection of the three dimensional distribution of the radio-pharmaceutical substance in the portion of the body, a representative layer 33 of voxels having N voxels is chosen as a reference to which analysis is "focused" on. Preferably, the layer is chosen to be at the effective distance H from the detector. Alternatively, the layer may be chosen at some inclination with respect to the surface of the detector or a specific curved layer. The physical dimensions of a bin, a voxel and a collimator orifice do not have to be equal, nor do these dimensions must be regular. The enhanced image could be formed by projecting the calculated distribution of the radio-pharmaceutical in the representative layer onto a two dimensional array of pixels in the enhanced image plan. In some cases such as the case of curved or irregular representative layer, some interpolation may be needed in order to perform the projection process. I case where the representative layer is a plane, divided to a regular grid, the projection from the represent layer voxels to the pixel of the enhanced image is trivial.

In a camera having several detectors, the chosen layer may be chosen not to be at equal distance from the detector (see for example FIG. 2) and thus, each detector will be associated with a different effective distance. Alternatively, in a dual detector camera, the layer may be chosen to be at the center of the camera, at equal distance from both detectors.

As a result of such discretization, the photons are binned according to their position on the detectors and a set of values $D_{i,k}$ (wherein i=1, . . . ,M. where M is the total number of bins) indicative of a number of photons acquired by the i-th bin, for any detector k (wherein k=1, . . . ,L, where L is the total number of detectors, or detector positions in case where a single detector is repositioned), is provided. Clearly, if the detector includes M crystals and each crystal is associated with a bin, then the step of additionally dividing of the detectors area onto M bins is unnecessary. If only one detector is used, the index k trivially assumes the value of 1. Alternatively, a detector could be placed in few positions k and the data collected while at each position will be labeled accordingly.

Alternatively or additionally, values $D_{i,k}$ may be grouped into plurality of sub-groups $D_{i,k,t}$ where t indicates the sub group. For example, the data acquired during the first half of the acquisition time could be used to form the sub-groups $D_{i,k,1}$ while data acquired during the second half of the acquisition time could be used to form the sub-groups $D_{i,k,2}$. Similarly, the acquisition time can be divided to any number of segments, optionally overlapping.

Alternatively or additionally, the data on each event can be stored in a file associated with additional information such as time of the event, detector location etc. This method of data saving known as "List Mode Acquisition" allows greater flexibility as data may be re-grouped or binned in various ways during post processing. Additionally, when the number of sub-groups is large, each of the arrays $D_{i,k,t}$ may contain small number of events and may in fact be sparse. Thus, a list mode acquisition may provide a more efficient way to store, access and process the data.

In the exemplary illustration of FIG. 2, detector 2a is equipped with collimator 10a establishing angles of incidence of gamma rays on the detector in a restricted range of 0 to $\alpha_a$ which is smaller than the corresponding angles of incidence $\alpha_b$ established by collimator 10b on detector 2b.

Further, a coupling between each bin of the detectors and each voxel of the portion of the body is established. As a result of the coupling, a matrix $P=\{P_{i,j,k}\}$ of weight values of the voxels of the portion of the body (wherein i=1, . . . ,M, j=1, . . . ,N and k=1, . . .,L) is constructed. For the rest of the discussion, the reference to the index k in the elements of the matrix P, and in the detector values D will be omitted.

Figure 4A:
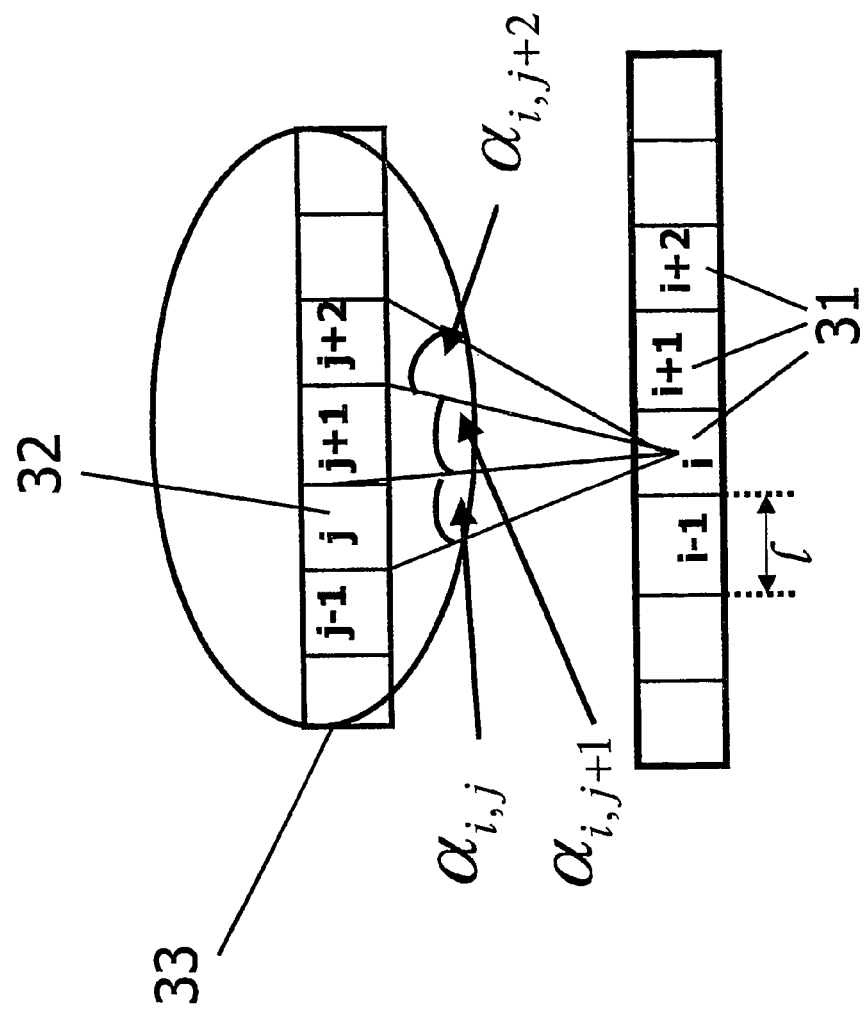
FIG. 4a illustrates a simplified diagram depicting an example for association between different elements (bins) of a detector and corresponding volumetric elements (voxels) in the patient's body in accordance with a preferred embodiment of the present invention.

FIG. 4a shows a simplified, two dimensional diagram depicting one example of the coupling between bins 31 having indices i, i+1, i+2, . . . and a voxel 32 having an index j, which results in weight values $P_{i,j}$, $P_{i+1,j}$, and $P_{i+2,j}$ that are functions of a set of angles $\alpha_{ij}$, $\alpha_{i+1j}$, $\alpha_{i+2j}$, . . . ,. In the case when collimators are used, a photon that emanated from voxel i and is within the angle of view of a given bin, may be absorbed by the walls of the collimator at that area. Therefore, the $P_{i,j}$ should be multiplied by the relative effective area of bin i as viewed from voxel j. (see, for example, C. E. Metz, F. B. Atkins and R. N. Beck, "The Geometric transfer function component for scintillation camera collimators with straight parallel holes," Phys. Med. Biol., 1980, v. 25, p. 1059-1070).

Optionally, the probability of a gamma photon to penetrate the thin collimator septa could be taken into account when calculating $P_{i,j}$.

Optionally, when more than one energy window is considered, the matrix element $P^E_{i,j}$ could depend on the energy window E so as to take into consideration the difference between the coupling coefficients of different energies. For example, when the radioactive isotope used emits gamma photons of few energy peaks, each of the energies would generally be associated with a different detector resolution, detector sensitivity, collimator septa penetration probability and different attenuation and scattering coefficients. One enhanced image could be obtained using all the data while associating the appropriate matrix element $p^E_{i,j}$ to each photon or alternately, few enhanced images could be obtained separately and optionally combined later.

Often a mixture of several different isotopes is present in the body at the time of the examination and it is advantageous to construct different images representing the distribution of the different isotopes. In that case, different matrix element $p^E_{i,j}$ could depend on the energies of the photons emitted by the several isotopes.

According to a more general example, P may be a matrix in which each of the matrix elements $P_{i,j}$ is a function of an average angle and possibly distance at which a detector bin having an index i is viewed from the voxel having an index j. Alternatively, the P may be a matrix in which each of the matrix elements $P_{i,j}$ is a function of an angle and possibly distance at which the detector bin having an index i is viewed from a center of the voxel having an index j.

Figure 4B:
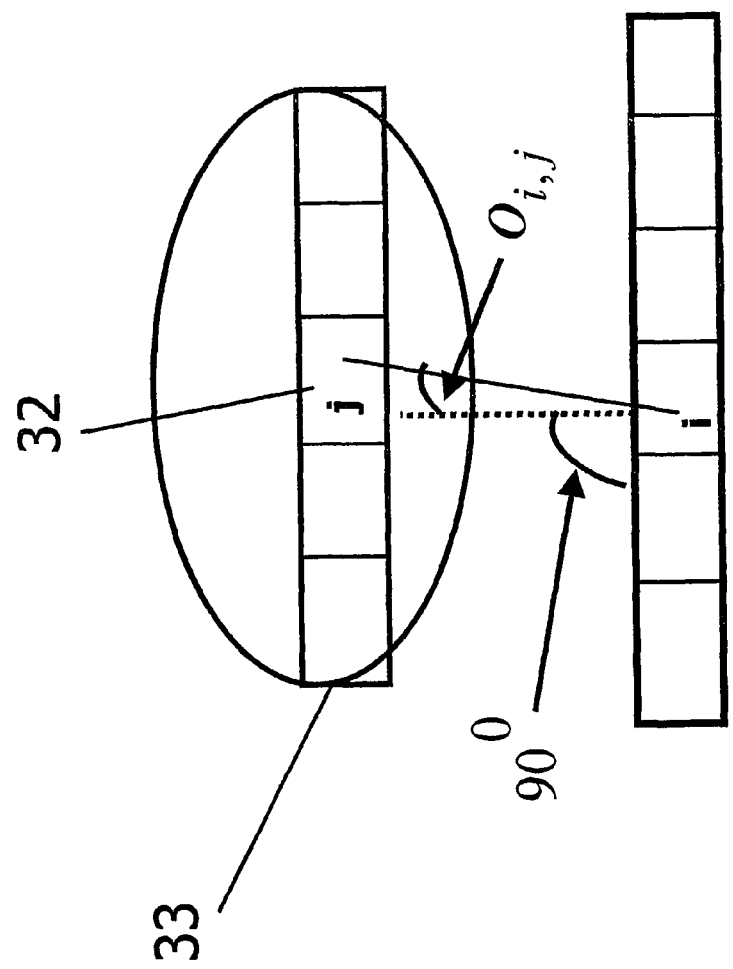
FIG. 4b illustrates a simplified diagram depicting another example for association between different elements of a detector and corresponding elements of patient's body in accordance with another preferred embodiment of the present invention.

FIG. 4b illustrates another example, in 2 dimensions, wherein P is a matrix in which its elements are presented by equation $$P_{i,j} = c\frac{l\cos\Theta_l}{z},$$

wherein $\Theta_i$ is the angle at which the detector's bin having an index i views the voxel having an index j, c is a constant, l is the length of the detector bin's side, z is the distance between the centers of the voxel having index j and the bin having index i. As yet another example, the value of the angle $\Theta_i$ may be an average angle of view from the bin having an index i into the voxel having an index j.

In some embodiments, the weights depend on the solid angle between a given point in a voxel and a given detector's bin, on the index k identifying detector position and on the distance of the voxel from the bin.

According to a more general example, P may be a matrix in which each of the matrix elements $P_{ij}$ is a function of an average angle and possibly distance at which a detector bin having an index i is viewed from the voxel having an index j. Alternatively, the P may be a matrix in which each of the matrix elements $P_{ij}$ is a function of an angle and possibly distance at which the detector bin having an index i is viewed from a center of the voxel having an index j.

When collimators are used, these weights are multiplied by the area of the bin that can be seen through the collimator from the point in the voxel. In other words: let $P_{i,j}^{bin}$ be the probability of a photon, emitted from voxel i, reaching the bin j on the detector with the absence of collimator. Since a photon from voxel i is traveling toward the bin j, must pass a collimator, let $P_{i,j}^{col}$ be the probability that the photon will not hit any collimator septa in his way to the bin j. By definition the probabilities $P_{i,j}^{bin}$ and $P_{i,j}^{col}$ are independent, thus the total probability of a photon emitted from voxel i, to hit the bin j which lies behind a collimator is given by $P_{i,j}=P_{i,j}^{bin} \cdot P_{i,j}^{col}$.

The elements of the matrix P may be modified to incorporate the attenuation effect, when attenuation map is available. The modification is such that the $P_{i,j}$ as described above, will take into account the attenuation terms that are associated with the voxels through which the ray emanated at voxel j pass to arrive at bin i. The voxels considered for calculation of the attenuation need not be in the chosen layer 33 (see, for example, D. L. Baiely, B. F. Hutton & P. J. Walker, *"Improved SPECT Using Simultaneous Emission and Transmission Tomography"*, J Nucl Med, 1987, 28: 844-851).

In order to derive voxel values $V_j$ of an image of the portion of the body and thereby to obtain a spatial distribution of the pharmaceutical substance indicating the functional information on this portion of the body, a mathematical model should be formulated and solved. Formulation of the mathematical model includes modeling a relation between the set of non-negative values $D_i$ and a set of unknown non-negative voxel values $V_j$ of the image (hence, a 'positive constraint').

As one example, the mathematical problem for deriving $V_j$ may be formulated as a set of algebraic equations $$D_i = \sum_{j=1}^{N} P_{i,j} V_j$$

with respect to each unknown value $V_j$ may be solved, wherein j=1, ..., N and i=1, ..., M. □ As it can be clear to a man of the art, the set of equations in a general form is:

$$D_i = \sum_{j=1}^{N} P_{i,j} V_j + E_i$$

i.e. also includes a set of measurement errors $E_i$

Their random nature of the data makes it necessary to add two ingredients to the setting of our problem:

A) a model of the nature of noise: depending on the application Poisson, Gaussian, or a mixture of Poisson and Gaussian might be used, though the current invention is not restricted to any of them B) An estimator for Vj: maximum likelihood, and maximum entropy are common choices, though the current invention is not limited to any of them.

As an example, the mathematical problem may be formulated as maximum likelihood with Poisson noise, and then solved for the unknowns, Vj, by means of the Expectation Maximization (EM) algorithm, or any other optimization algorithm (see, for example, the technique of L. A. Shepp and Y. Vardi, *"Maximum likelihood reconstruction for emission tomography,"* IEEE Trans Med. Imaging, 1982, v. 1, p. 113-122, or K. Lange and R. Carson, *"EM reconstruction algorithm for emission tomography,"* J. Comput. Assist. Tomogr., 1984, v. 8, p. 306-316).

As yet another example, the mathematical problem may be formulated as least squares (possibly weighted least squares) with Gaussian or Poisson noise, and then solved for the unknowns, Vj, by means of singular value decomposition, or any other optimization algorithm such as the steepest decent algorithm. (references for these methods, see for example William H. Press et al, *"Numerical Recipes in C++"*, Cambridge University Press, Chapter 2,)

In exemplary embodiment of the invention, the optimization problem can formulated as a statistical model of the emission process for estimating image data. According to the model, the number of photons $V_j$ that are emitted from a voxel with an index j obeys the Poisson distribution $$P(V_j = n) = \frac{e^{-\lambda(V_j)} \lambda(V_j)^n}{n!},$$

wherein $P(V_j=n)$ is the probability of having n events of photon emissions in the j-th voxel, and $\lambda(V_j)$ is the unknown mean value of the Poisson distribution. Further, the number of photons $D_i$ that are acquired by the i-th bin also obeys the Poisson distribution with mean value of the distribution $\lambda(D_i)$. The random variables $V_j$ and $D_i$ as well as their respective mean values $\lambda(V_j)$ and $\lambda(D_i)$ are, correspondingly, related via the following equations $$D_i = \sum_{j=1}^{N} P_{i,j} V_j \text{ and } \lambda(D_i) = \sum_{j=1}^{N} P_{i,j} \lambda(V_j).$$

Thus the optimization problem is used to estimate the mean value $\lambda(V_j)$ of the Poisson random variables $V_j$, using the $D_i$ values measured by the detector. For example, one conventional statistical approach for determination of $V_j$ is to find a maximum of the likelihood function $$L[\lambda(D_i)] = \prod_{i=1}^{M} \frac{e^{-\lambda(D_i)} \lambda(D_i)^{D_i}}{D_i!},$$

with respect to the unknowns $V_j$.

As yet another example, the mathematical problem may be formulated as a Bayesian optimization problem, in which a likelihood function is utilized together with a penalty function known per se. (See for example, P. J. Green, Bayesian reconstruction from emission tomography data using a modified EM algorithm, IEEE Trans Med. Imaging, 1990, v. 9, p. 84-93, or P.J. Green, *On the use of the EM algorithm for penalized likelihood estimator*, J. Roy. Statist. Soc. (B), 1990, 52:443-452, or D. Geman and G. Reynolds, *Constraint Restoration and the Recovery of Discontinuities*, IEEE trans on Pattern Analysis and Machine Intelligence, 1992, v. 14, p. 367-383.) This optimization problem should be solved for deriving the unknown values $V_j$. As an example, but not limited to, a general form of the Bayesian optimization problem can be written as follows: V=arg max{$L[\lambda(D_i)]+\alpha F(V_j, V_k)$}, where $\alpha$ is the weight that is given to the prior function F.

For instance the penalty function may be chosen in the form of $$F(V_j, V_k) = \sum_{j,k} (V_j - V_k)^2,$$

wherein the sum is taken over two neighboring voxels having indices j and k. Such a penalty function expresses some prior knowledge about the smoothness characteristics of the reconstructed image. Other penalty functions, which preserve discontinuities are more adequate for planar image enhancement.

As it can be clear to a man of the art, the choice of the optimal collimator acceptance angle utilized is guided by the trade-offs between resolution and sensitivity that can be tolerated. Factors, for instance, such as desired acquisition time, resolution, sensitivity, noise characteristics should also be taken into account. This choice dictates whether to use collimators, if so what are their characteristics, or alternatively use septa or do not use collimators at all. When using collimators for example, the characteristics of the collimator, such as the hole's dimensions, are determined by the accepted incidence angle, as well as by other factors. The accepted incidence angle itself is determined by the desired resolution and sensitivity. Hence, practical solutions will depend on the factors mentioned above and can be optimized accordingly.

For example, collimator characteristics may be guided by the priority to have a high sensitivity image rather than high resolution in renal imaging, cardiac first pass imaging and Gallium scan for staging Lymphomas or evaluation of treatment of malignancies. In contrast, bone images, lung ventilation and gastric emptying studies may require high resolution because of the nature of fine structures.

Image enhancement in accordance with some preferred embodiments of the present invention enables obtaining high resolution images with a collimator of higher sensitivity then used in the art with acceptance angles exceeding what is currently used in the art such as exceeding 5 or even 10 degrees. The added performance could be traded off as to shorten acquisition time, obtaining images of higher quality, using lower activity of radio-pharmaceutical or combination of these advantages.

As known to a person skilled in the art, collimator 10 to be used in a preferred embodiment of a gamma camera in accordance with the present invention may be a collimator having hexagonal holes arranged in a beehive arrangement.

In another preferred embodiment of a gamma camera in accordance with the present invention, collimator 10 may be a collimator having circular holes arranged in a beehive arrangement, and separating septa. In this embodiment the collimator consists of hexagonal cells, each cell having a circular hole. Optional separating septa—a pair in this embodiment—limit the field of view of the collimator, and serve as shields against photons that went astray. In this embodiment the septa are generally mounted along the lateral axis of the collimator, but may be mounted along any desired axis of the collimator according to the particular desired enhanced field of view.

Alternatively collimator holes may have oval shape. The collimator holes may be symmetric, such as circular, square or hexagonal shaped holes. Alternatively the collimator holes may be non-symmetric or non-uniform in terms of shape or size or both. The collimator holes may be of different dimensions along different axes, such as ellipse or rectangular shape holes, and these holes may have cylindrical, conic or other converging shapes. In an alternative embodiment of the camera of the present invention, the camera is provided with a collimator having direction bias holes favoring detection from a predetermined lateral direction and limiting detection from other directions.

When applying image-enhancing algorithm in accordance with the present invention, several sets of parameters such as effective distance, penalty functions or number of iterations could be chosen and applied to parts or the entire data set. The resulting enhanced images may be displayed as an image gallery, or sequentially or combined into one or more combined images, for example by weighted averaging. For example, when using a dual detector camera, the image constructed from the two detectors could be combined or displayed side by side. Alternatively, several enhanced images may be incorporated by selecting values from each image according to some criteria and showing them on a single or several images. For example, the criteria for selection could be the maximum value among the values corresponding to the same pixel in the several enhanced images.

When sections of the body are known to have several specific organs at several effective distances, several enhanced images according to the several effective distances may be created and combined by selecting and joining portions of the several; enhanced images. Similarly, a non-uniform map of weights could be used to perform weighted averaging of the several images where in each section of the combined image, greater weight is given to the enhanced image, which has higher image quality. Image quality of a section of an enhanced image could be determined a-priory or judged by statistic tests such as noise, quality of fit or combination of several statistical tests, such as the value of the penalty function when employed. Similarly, images taken by several detectors or using several collimators 10 or from several positions in relative to the body may be combined to form a combined image. For example, a high-resolution collimator could be used on one detector and high-sensitivity collimator on another detector, both imaging the same portion of the body. Image derived from high-resolution collimator may primarily be used for defining the boundaries of a specific organ, while an image derived from the high-sensitivity collimator may primarily be used for determining the activity or the dynamics of the activity within the specific organ.

In iterative processing of data, it is sometimes advantages to use a subset of the total data in each iteration Haudson H. M., R. S. Larkin, *"Accelerated Image Reconstruction Using Ordered Subsets of Projection Data"*, IEEE Transactions on Medical Imaging, Vol. 13, NO 4, December 1994.

In planar imaging, subsets may be acquired sequentially one after the other. Alternatively or additionally, data could be divided into subsets according to the detector or the position of the detector when the datum was acquired.

Iterative processing may be performed concurrently with data acquisition by using part of the data already acquired as a subset for the enhancement algorithm while the gamma camera continues to acquire additional data. The advantage of starting the processing during data acquisition is that the final enhanced image is obtained short time after the end of the acquisition. Thus, the operator may judge the quality of the image and decide whether additional imaging is required before the patient is taken away.

Often, the data subset may be sparse, that is few of most of the bins may not contain any counted photons. In these situations, calculations could be performed only for the bins in which at least one photon was counted. The order of calculations may then be set to the order in which the photon were counted rather then a methodical raster scan of the bins. The smaller the size of a bin, the more unlikely it is that no photon will be counted in a bin in a given time. Thus, using photon-oriented ordering of the iterative processing is advantageous when bin size is small and the number of counted photons is limited. A list of the counted photons, each with associated information about the location of the photon on the detector and optionally information about the position of the detector and optionally about the energy of the photon may be stored in the data analysis computer or a data storage device and be used as data set for the image enhancement.

The effect of scattering of gamma photons within the body could be taken into account when calculating the matrix $P_{i,j}$ by performing scattering calculations of the possible trajectories of a photon from voxel j to bin i.

In a Compton scattering event, a photon is deflected from its original direction by interaction with an electron. The larger the angle of deflection—the more energy the deflected photon loses in the scattering event. Some of the photons may be deflected by small angle and their energy loss may be too small to be detected by due to limited energy resolution of the detector. When a single energy window is used per energy peak, the estimated photon energy is compared and the photon is rejected if its energy falls outside the energy window. This may result in false rejection of several photons and false acceptance of other photons. When additional information about the estimated energy of a photon is available, a matrix $P^E_{i,j,dE}$ may be constructed where E is the initial photon energy in multi-peak isotope or when more than one isotope is used, and dE is the energy difference between the measured photon energy and the assumed initial energy of that photon (dE may be positive due to detector inaccuracy).

Both analytical or numerical calculation of $P^E_{i,j,dE}$ are possible.

In a Monte-Carlo calculation of $P^E_{i,j,dE}$, one starts at a source voxel "j" and follows random photon trajectories as they are subjected to scatter and absorption in the body before reaching the destination bin "i". Smoothing and averaging of $P^E_{i,j,dE}$ could be done as it is expected to be a small and smooth function. Enhancement algorithms may be used to create several enhanced images each image based on photons selected by their measured energy. These enhanced images may later be combined into a combined image.

Alternatively or additionally, information about the measured energy of a photon as determined by the detector may be used to as an indication to the ability of that photon to provide information on the distribution of radio-pharmaceutical within the body. A photon weight is given to each photon counted based on the energy difference dE. As en example, a counted photon with energy close to the energy window cut-off may be considered to have 50% probability to be a scattered photon and will be counted as having a weight of 0.5.

Alternatively, data from photons with measured energy below the energy peak can be used to create an image indicative to the effect of scattered photon on the enhanced image and used to correct the enhanced image by subtraction.

Artifact related to collimator 10 could be effectively removed by calculating matrix element $P_{i,j}$ taking into account the position of collimator 10 relative to bin i and voxel j as is the case when collimator 10 is a collimator with bore size close to or larger then the spatial resolution of the detector.

Other artifacts related to system non-uniformities could also be corrected by adjusting the values of elements in matrix P. For example, collimators are often made with irregularities, which cause inconsistent sensitivity and resolution between different sections of the same collimator. Similarly, PMT (photomultiplier tubes) based detectors exhibit pattern of variations in their spatial resolution, energy resolution and sensitivity. Crystal 6 may also exhibit irregularities and variations between the crystals in a multi-crystal detector.

These and other artifacts may effectively be eliminated by acquiring data in several locations and combining the data or the enhanced images.

In order to assist the operator in locating features in the enhanced image, the image could be combined or overlaid with an image acquired by another imaging modality such as X-Ray, CT or MRI and processed to be displayed in substantially the same scale.

Figure 5A:
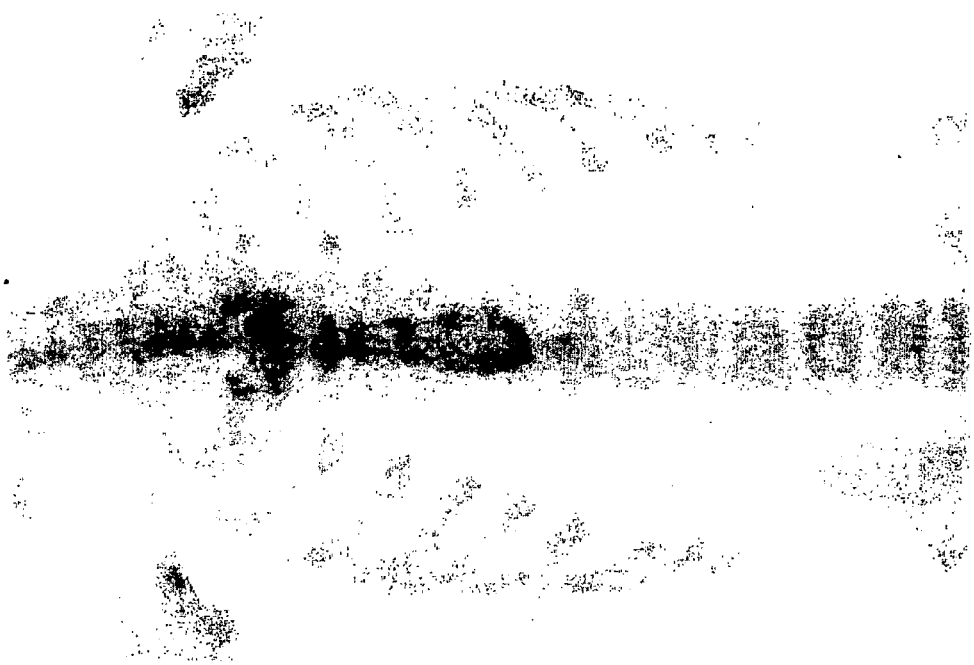
FIG. 5a illustrates a clinical image of a patient's torso taken in standard planar technique.
Figure 5B:
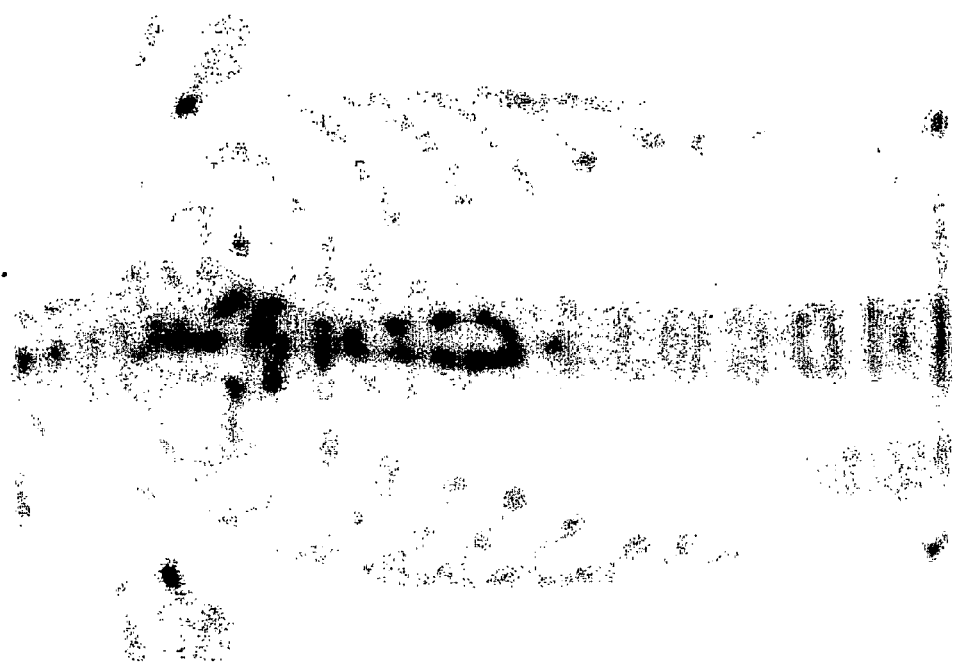
FIG. 5b illustrates a clinical image of the same patient's torso, taken in accordance with a method for enhanced planar single photon emission imaging in accordance with a preferred embodiment of the present invention.

FIGS. 5a and 5b illustrate the advantage of image enhancement in accordance with the present invention. In FIG. 5a a conventional image is shown, representing raw data as collected by the detector. This is a bone imaging of a patient who was administered pharmaceutical labeled with Tc isotope. Image 5a was used as input data for the enhanced image shown in FIG. 5b. The enhancing procedure for this specific image included a Poisson likelihood function, optimized by the EM algorithm using 4 iterations. Other modeling and optimization process were found to be successful in the enhancement of planar images. As can be seen in the enhanced image 5b, the vertebra are better separated and structures are better defined.

While the invention has been described with reference to certain exemplary embodiments, various modifications will be readily apparent to and may be readily accomplished by persons skilled in the art without departing from the spirit and scope of the above teachings.

It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. The terms "comprise", "include" and their conjugates as used herein mean "include but are not necessarily limited to"

The invention claimed is:

1. A method of enhancing quality of a planar image acquired by a detector in single photon emission imaging of a portion of a body or at least one specific organ or volume of interest located within the portion of the body, the portion of the body administered with radio-harmaceutical substance radiating gamma rays, the method comprising:

selecting, for each pixel of the acquired planar image at least one selected distance from the detector, forming a set of effective distances, said set having at least one effective distance;

calculating, for each pixel, weight values utilizing acceptance angles of the gamma camera detector and the said at least one selected distance of the set of effective distances;

constructing a two dimensional image of a spatial distribution of the pharmaceutical substance within the portion of the body by mathematically analyzing said data in conjunction with the weight values.

2. The method of claim 1 wherein the step of calculating weights values takes into account the probability of a photon to be attenuated within the body.

3. The method of claim 1 wherein the step of calculating weights values takes into account Compton scattering within the body of the patient 4. The method of claim 1, wherein mathematically analyzing said data is done using an iterative algorithm.

5. The method of claim 1, wherein said at least one selected distance of the set of effective distances is selected utilizing a priory, knowledge of human anatomy.

6. The method of claim 1, wherein said at least one selected distance of the set of effective distances is selected utilizing information relevant to the patient.

7. The method of claim 1, wherein said at least one selected distance of the set of effective distances is selected utilizing single photon emission image taken from another detector position.

8. The method of claim 1, wherein said at least one selected distance of the set of effective distances is selected utilizing a medical imaging modality other than single photon emission imaging.

9. The method of claim 1 wherein said data comprises data obtained from a plurality of views, and wherein at least two views are acquired using dissimilar collimators.

10. The method of claim 1, wherein the set of effective distances, or a portion thereof, defines a plane.

11. The method of claim 1, wherein the set of effective distances, or a portion thereof, defines a curved surface.

12. The method of claim 1, wherein the detector is adapted to detect emitted photons having incident angles in the range of 0 to more than 5 degrees.

13. The method of claim 1 wherein said analysis comprises the steps of:
   (a) dividing an area of the detector facing the body into M bins;
   (b) dividing the portion of the body into N voxels;
   (c) providing a set of values $D_i$ (wherein i=1, . . . ,M) reflective of the number of photons acquired by each bin;
   (d) constructing a matrix P having matrix elements $P_{ij}$ of weight values of the voxels of the portion of the body (wherein i=1, . . . ,M and j=1, . . . ,N), the matrix P setting a relation between each bin of the detector and each voxel of the portion of the body;
   (e) modeling a relation between said set of values $D_i$ and a set of voxel values $V_j$ corresponding to a selected distance from the set of effective distances and deriving said set of voxel values $V_j$ of said image.

14. The method of claim 13 wherein at least two of said bins are of unequal size.

15. The method of claim 13 wherein at least two of said voxels are of unequal size.

16. The method of claim 13 wherein dimensions of said bins are unequal to the dimensions of pixels in the obtained image.

17. The method of claim 1 further comprising obtaining a plurality of planar images each utilizing a different set of weights.

18. The method of claim 17 wherein at least two obtained images are combined to form a single image.

* * * * *